US009320986B2

(12) United States Patent
Der et al.

(10) Patent No.: US 9,320,986 B2
(45) Date of Patent: Apr. 26, 2016

(54) METHANOL PURIFICATION METHOD AND APPARATUS

(75) Inventors: Bruce Der, Vancouver (CA); Allan Stewart Jensen, Vancouver (CA)

(73) Assignee: A.H. Lundberg Systems Limited, Vancouver, British Columbia (CA)

( * ) Notice: Subject to any disclaimer, the term of this patent is extended or adjusted under 35 U.S.C. 154(b) by 912 days.

(21) Appl. No.: 13/201,206

(22) PCT Filed: Feb. 12, 2009

(86) PCT No.: PCT/CA2009/000172
§ 371 (c)(1),
(2), (4) Date: Aug. 11, 2011

(87) PCT Pub. No.: WO2010/091492
PCT Pub. Date: Aug. 19, 2010

(65) Prior Publication Data
US 2011/0306807 A1    Dec. 15, 2011

(51) Int. Cl.
| | | |
|---|---|---|
| *B01D 3/00* | (2006.01) | |
| *B01D 3/02* | (2006.01) | |
| *C07C 29/78* | (2006.01) | |
| *B01D 5/00* | (2006.01) | |
| *B01D 3/14* | (2006.01) | |
| *B01D 53/00* | (2006.01) | |
| *D21C 11/06* | (2006.01) | |

(52) U.S. Cl.
CPC .............. *B01D 5/0063* (2013.01); *B01D 3/143* (2013.01); *B01D 5/0012* (2013.01); *B01D 53/002* (2013.01); *D21C 11/06* (2013.01); *B01D 2256/24* (2013.01); *B01D 2257/80* (2013.01); *B01D 2258/05* (2013.01)

(58) Field of Classification Search
CPC .......................................................... B01D 1/26
See application file for complete search history.

(56) References Cited

U.S. PATENT DOCUMENTS

| | | | |
|---|---|---|---|
| 3,807,479 A | 4/1974 | Brannland et al. | |
| 4,137,134 A | 1/1979 | Suominen et al. | |
| 5,718,810 A * | 2/1998 | Robbins et al. | 203/76 |
| 5,830,314 A | 11/1998 | Mattsson | |
| 5,989,394 A | 11/1999 | Johyansson et al. | |
| 6,217,711 B1 * | 4/2001 | Ryham et al. | 203/26 |

FOREIGN PATENT DOCUMENTS

| | | |
|---|---|---|
| CA | 1088957 | 11/1980 |
| SE | 524106 | 6/2004 |

OTHER PUBLICATIONS

A.H. Lundberg Systems Ltd., et al., "International Search Report and Written Opinion," Int'l Patent Application No. PCT/CA2009/000172, filed Feb. 12, 2009 (Apr. 9, 2009).

* cited by examiner

*Primary Examiner* — Duane Smith
*Assistant Examiner* — Cabrena Holecek
(74) *Attorney, Agent, or Firm* — Sunstein Kann Murphy & Timbers LLP

(57) ABSTRACT

The invention relates to a method and apparatus to recover and purify methanol from gases produced in the digester during the kraft pulping process. The gas is typically recovered as a foul gas (called stripper off gas or SOG) comprising methanol, water and various other contaminants. The gas is then treated with successive decanting and distillation steps to remove impurities, thereby producing highly purified methanol.

10 Claims, 4 Drawing Sheets

METHANOL PURIFICATION METHOD AND APPARATUS

FIELD OF THE INVENTION

This invention relates to a method and apparatus to recover purified methanol stripped from a foul gas stream.

BACKGROUND OF THE INVENTION

Methanol is formed as a by-product of the kraft pulping process, when the hydroxyl on reacts with a lignin methoxyl group:

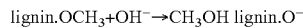

Depending on the mill configuration, up to 90% of the methanol generated in the digester can be captured in the foul condensate from the digester and evaporator areas. The foul condensate is typically treated in a steam stripping system, where up to 95% of the methanol can be removed from the foul condensate and captured in the overhead vapours from the stripping process. The concentrated gas stream is often referred to as stripper off gas (SOG).

The SOG is then usually disposed of through thermal oxidation in a lime kiln, power boiler, recovery boiler, or dedicated incinerator. The SOG typically consists of about 40 to 70 wt % methanol, 5 to 10 wt % non-condensable materials, including sulphur compounds, and the balance water vapour.

Waste SOG can be burned as a replacement for fossil fuels. However, the value of SOG as a fuel depends on the amount of water vapour that it contains. Natural gas provides 50.5 MJ/kg (37.2 MJ/m$^3$) heat of combustion, pure methanol provides 22.7 MJ/kg, and SOG containing 70 wt % methanol provides the equivalent of about 21.9 MJ/kg. The SOG provides less heat because the entrained water vapour must first be heated up to combustion temperature.

Chlorine dioxide is used in the pulp bleaching process; grade AA methanol (99.85 wt %) is used to manufacture $ClO_2$. In a well-run mill, a methanol purification system would preferably be able to produce sufficient amounts of purified methanol for the demands of the $ClO_2$ process, as well as some purified methanol for external sale. If a substantial portion of the methanol in the SOG can be recovered and purified to an industrial grade AA product, the methanol produced in a typical kraft pulping process could be worth as much as four and a half times more as a commodity than as a fuel.

There are numerous methanol purification systems in operation. Most such systems use some form of distillation to separate methanol from other compounds. See for example, U.S. Pat. No. 5,718,810 to Robbins and U.S. Pat. No. 6,217,711 to Ryham et al. Canadian Patent No. 1,0888,957 to Suokas et al., uses a combination of distillation steps and acid or alkaline oxidating treatments to separate the various fractions. Distillation separates the components of a solution by partial vapourization of the mixture and separate recovery of vapour and residual liquid. The more volatile constituents of the original mixture are obtained in increased concentration in the vapour, while less volatile components remain in greater concentration in the liquid residue. Distillation columns may be designed using trays, structured packing, or random dumped packing. Due to restricted access, for small columns below about 750 mm diameter, random dumped packing is preferred.

However, methanol recovered from a kraft pulping process has several unique characteristics that inhibit separation by distillation.

Typically, significant quantities of dimethyl disulphide are present in the crude methanol produced during the kraft pulping process. The presence of an azeotrope between methanol and dimethyl disulphide requires that the methanol content in the SOG be no higher than approximately 40 wt % to ensure separation. Control of the foul condensate steam stripping system, in terms of both the quantity and quality of SOG produced, can reduce the impact of azeotropes of dimethyl disulphide. Many existing stripping systems include a reflux condenser integrated with the multiple effect evaporators; see for example U.S. Pat. No. 4,137,134 to Suominen et al., U.S. Pat. No. 3,807,479 to Brannland et al., and U.S. Pat. No. 5,830,314 to Mattsson. Unfortunately, in this arrangement, control of the stripping system may be compromised because any fluctuations in evaporator operation will ripple through the stripping system, unpredictably affecting SOG quantity and quality.

Further, contaminants including ionizable sulphur compounds such as hydrogen sulphide and methyl mercaptan are produced during the pulping process. These compounds can dissociate under certain conditions, making them all but impossible to remove from SOG by simple distillation. As can be seen in FIG. 1, hydrogen sulphide ($H_2S$) begins to dissociate at a pH above about 6, while methyl mercaptan (MM) begins to dissociate at a pH above about 9. In their dissociated form, these compounds do not exert a vapour pressure and therefore can not be removed by distillation. Controlling the pH of the liquid phase in the distillation column is therefore an effective way to remove these compounds in a distillation process.

As condensed SOG typically has a pH of about 9 to 10, an acid, such as sulphuric acid, may be metered to the appropriate distillation column to lower the pH in the system. However, the acid cannot simply be added to the liquid feed to the column as it will react with any ammonia present in the system, producing ammonium sulphate. This is known as fouling the column and is to be avoided. U.S. Pat. No. 5,989,394 to Johansson et al. describes a process in which an acidifier is introduced to a stripping column above the admission point of the liquid being purified, or alternatively is added to the liquid feed directly. However, Johansson is concerned with producing a relatively purified condensate stream, rather than removal and high level purification of methanol from the liquid feed stream and does not seem to be concerned with fouling the column.

It is therefore an object of the invention to provide a method and apparatus to recover and purify methanol stripped from a foul gas stream that overcomes the foregoing deficiencies.

In particular, it is an object of the invention to provide a method and apparatus to recover and purify methanol to a high degree, allowing methanol to be used within a kraft pulping process and to allow excess methanol to be sold, rather than destroyed.

These and other objects of the invention will be appreciated by reference to the summary of the invention and to the detailed description of the preferred embodiment that follow.

SUMMARY OF THE INVENTION

The invention relates to a method and apparatus to recover and purify methanol from gases produced in the digester during the kraft pulping process. The gas is typically recovered as a foul gas (called stripper off gas or SOG) comprising methanol, water and various other contaminants.

Stripper off gas is stripped from the digester and evaporator areas of the pulping process; the SOG then passes, at a controllable flow rate to a dedicated condensing means, where volatile components are boiled off and vented to an incineration system, while the condensate drains to a topping red oils removal means, such as a decanter. Heavy contaminants that are immiscible in the solution are decanted and recovered separately. The underflow is moved to a first distillation means, such as a topping column and heated. Acid is added to the mid-point of the topping column to lower the pH of the solution without allowing the acid to react with ammonia in the feed. Volatile components are returned to the condensing means, while the underflow moves to a surge tank, which may be used to stabilize the flow and concentration of the feed to the rectification section.

The rectification section may comprise one or two columns. The feed is introduced near the top of the bottoms section of the column, and moves down through the packing in the column, countercurrent to the stripping steam flow. Vaporized methanol moves up through the top section of the column, and any impurities are removed as the overhead vapor flow. Water and other less volatile components form the underflow, while fusel oils are drawn off in a side stream. Purified methanol is drawn off and passed to a methanol cooler for condensation and storage. The methanol is at least 99.85 wt % pure.

Alternatively, the bottoms section and the top section may each be a separate column. The feed is introduced near the top of the bottoms column, and moves down through the packing in the column, countercurrent to the stripping steam flow. Vaporized methanol is removed as the overhead vapor flow. Water and other less volatile components form the underflow, while fusel oils are drawn off in a side stream. The methanol vapor is passed to the rectification top column, where it is distilled again. Condensate from the rectification top column is returned to the rectification bottoms column, while vapors are collected and condensed before being vented to the incineration system. Purified methanol is drawn off and passed to a methanol cooler for condensation and storage. The methanol is at least 99.85 wt % pure.

In one aspect, the invention comprises a method to recover and purify methanol from a stripped off gas stream, comprising the steps of: obtaining, at a controlled rate, a foul gas feed comprising no more than approximately 40 wt % methanol; condensing the foul gas feed; removing immiscible contaminants from the condensed foul gas feed; heating the condensed foul gas feed in the presence of an acid to evaporate volatile components, leaving a contaminated methanol feed, the acid being supplied at an entry point below an input point of the condensed foul gas feed; refining the contaminated methanol feed by heating to evaporate methanol from the contaminated methanol feed; and further refining the evaporated methanol by heating to evaporate remaining volatile components and to produce purified methanol and impure condensate. The purified methanol may be cooled and collected for storage. The condensate may be recycled to the step of refining the contaminated methanol feed.

In a further aspect, excess foul gas may be diverted to a disposal system prior to the condensing step.

In yet a further aspect, fusel oils may be stripped from the contaminated methanol feed during the refining step.

In further aspect, the invention may comprise the further step of storing the contaminated methanol feed prior to refining the contaminated methanol feed.

In a further aspect, the immiscible contaminants may be removed by decanting the immiscible contaminants.

In another aspect, the invention comprises an apparatus to recover and purify methanol from a stripped off gas stream, comprising: condensing means to receive and condense a controlled amount of stripped off gas comprising no more than approximately 40 wt % methanol; decanting means to remove immiscible contaminants from the condensed gas; first distillation means comprising upper and lower sections, to receive the condensed gas in the upper section, and to heat the condensed gas in the presence of acid received in the lower section, to evaporate volatile components, leaving contaminated methanol; a first refining section to evaporate methanol from the contaminated methanol; and a second refining section to evaporate and condense impurities from the evaporated methanol, producing purified methanol. Means may also be provided to capture and condense the purified methanol for storage In a further aspect, the apparatus of the invention may comprise storage means to store the contaminated methanol prior to entering the first refining section.

In a further aspect, the apparatus of the invention may comprise means to remove fusel oils from the contaminated methanol.

In another aspect, the first distillation means of the apparatus of the invention may comprise a topping column. The topping column may further comprise a reboiler to recycle part of the contaminated methanol.

In yet another aspect, the first and second refining sections of the apparatus of the invention may comprise a second distillation means. The second distillation means may comprise a rectification column, or first and second rectification columns.

In a further aspect, the apparatus of the invention may comprise means to divert excess gas to a disposal system prior to entering the condensing means.

The foregoing was intended as a broad summary only and of only some of the aspects of the invention. It was not intended to define the limits or requirements of the invention. Other aspects of the invention will be appreciated by reference to the detailed description of the preferred embodiment and to the claims.

The inventors thank Alberta-Pacific Forest Industries Inc. for its continued interest in this work and for its assistance in testing the system.

BRIEF DESCRIPTION OF THE DRAWINGS

The preferred embodiment of the invention will be described by reference to the drawings in which.

DETAILED DESCRIPTION OF THE INVENTION

Figure 1:
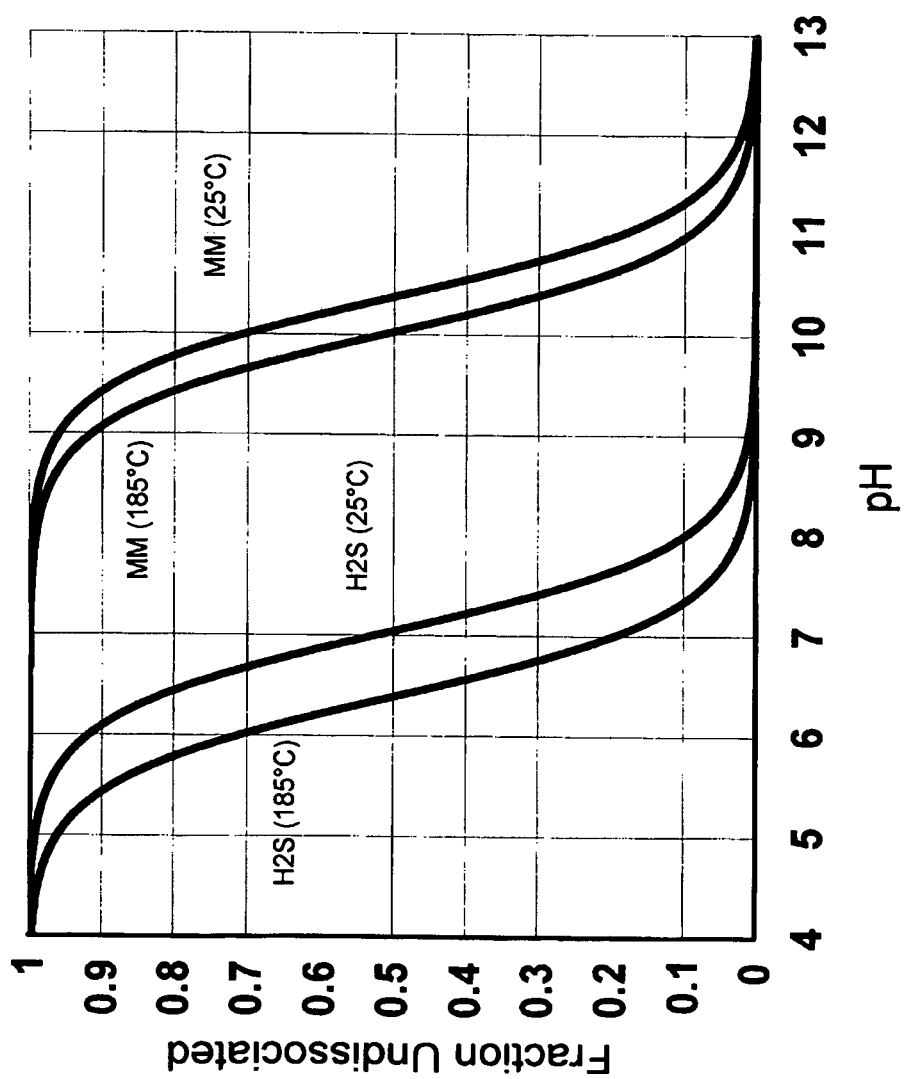
FIG. 1 is a graph showing the dissociation fractions for hydrogen sulphide and methyl mercaptan at various pH levels.
Figure 2:
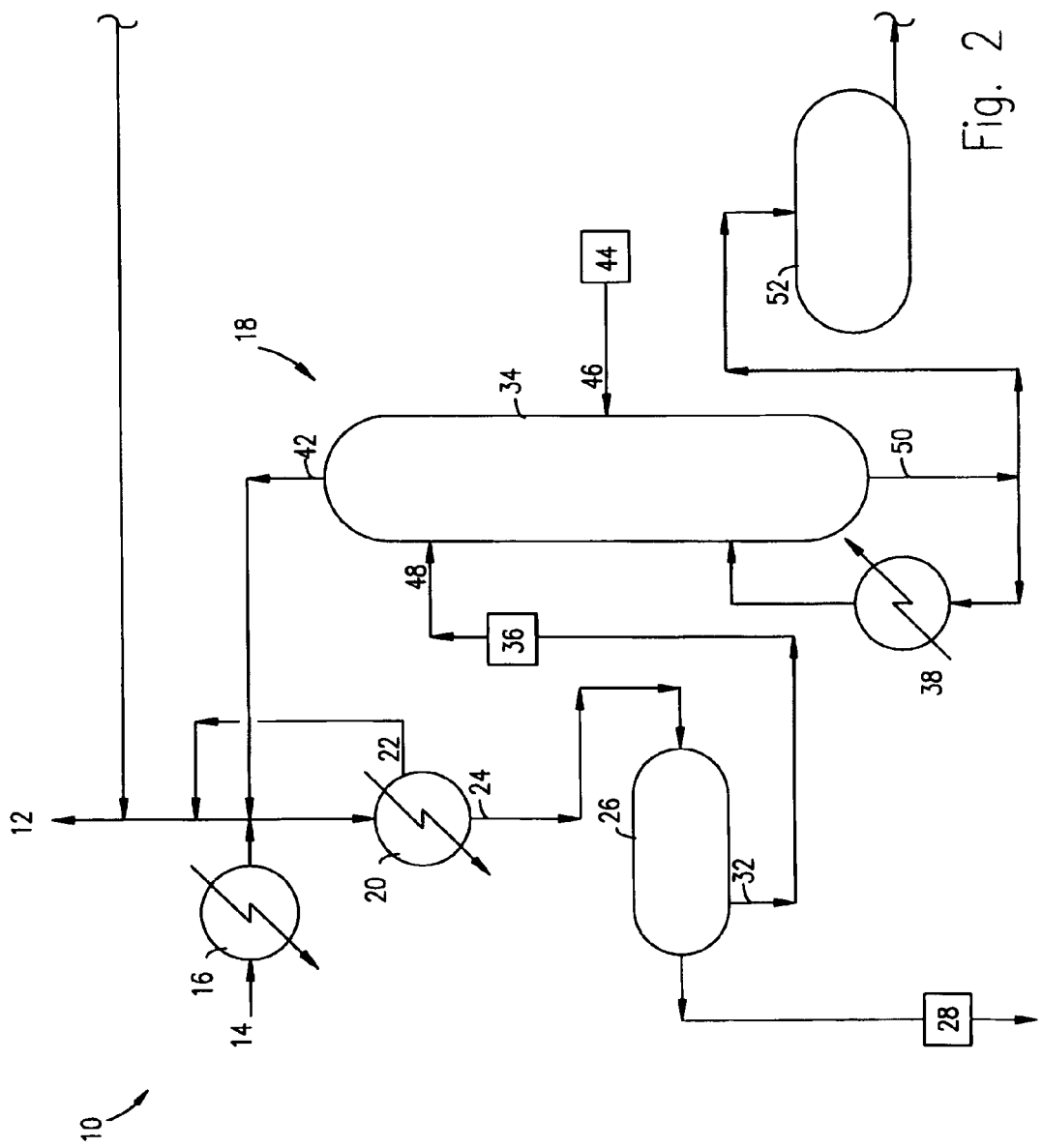
FIG. 2 is a schematic of the topping section of the invention.

Stripper off gas (SOG), typically containing about 40 to 70 wt % methanol, is produced in an existing foul condensate steam stripping column. The SOG is directed to a methanol purification system 10, being diverted from a kiln, boiler, incinerator or other incineration system 12, as shown in FIG. 2.

Vapour 14 from the existing stripping column is introduced to a dedicated reflux condenser 16; this vessel may be of any suitable type, such as a falling film type shell and tube evaporator effect. The heat from the stripping system may be utilized in the evaporator system, but use of a dedicated vessel allows sufficient control over the system to ensure stable qualities and quantities of SOG are produced under all evaporator operating conditions. Pressure is maintained by throttling the flash vapour from the system.

SOG is introduced to the methanol purification system 10 at a controlled flow rate, with any excess gas being diverted to the incineration system 12. This helps to maintain the methanol entering the purification system 10 at an optimal content of approximately 40 wt % or less.

The topping column system 18 strips out low boilers and non-condensables from the SOG, including malodorous sulphur compounds, ammonia, and some ethers, ketones and aldehydes. When SOG is introduced to the topping reflux condenser 20, the low boilers and non-condensables are vented 22 back to the incineration system 12 while the condensate is drained 24 to the topping red oils decanter 26.

Topping red oils pump 28 moves the decanted red oils to a turpentine recovery system (not shown), if available. The underflow 32 from the decanter 26 is moved to the topping column 34 by any suitable means, such as topping reflux pump 36. A topping reboiler 38 may be used to provide heat to the topping column 34, evaporating the volatile contaminants in a stream 42, which can be returned to the topping reflux condenser 20 or otherwise disposed of.

Sulphuric acid may be added to topping column 34 by any suitable means, such as feed pump 44. Preferably the acid is added about the mid-point of the column, or at any rate at an entry point 46 below the input point 48 of the condensed underflow feed from the topping reflux pump 36. The separation between the feed input point 48 and the acid entry point 46 allows any highly volatile ammonia present in the underflow feed to be stripped out in the upper section of the topping column 34 before it has a chance to react with the acid, thereby avoiding the formation of ammonium sulphate precipitates. The acid reduces the pH in the lower section of the topping column 34, releasing dissociated hydrogen sulphide and methyl mercaptan, which will rise to the upper section of topping column 34, where it can be removed as part of volatile contaminant stream 42.

The underflow 50 from the topping column 34 flows to the surge tank 52, with some being recycled to topping reboiler 38. As the flow and concentration of SOG can vary significantly depending on the operation of the existing stripping system, the surge tank can smooth out the flow and concentration of the feed to the methanol rectification column system 54.

Figure 3:
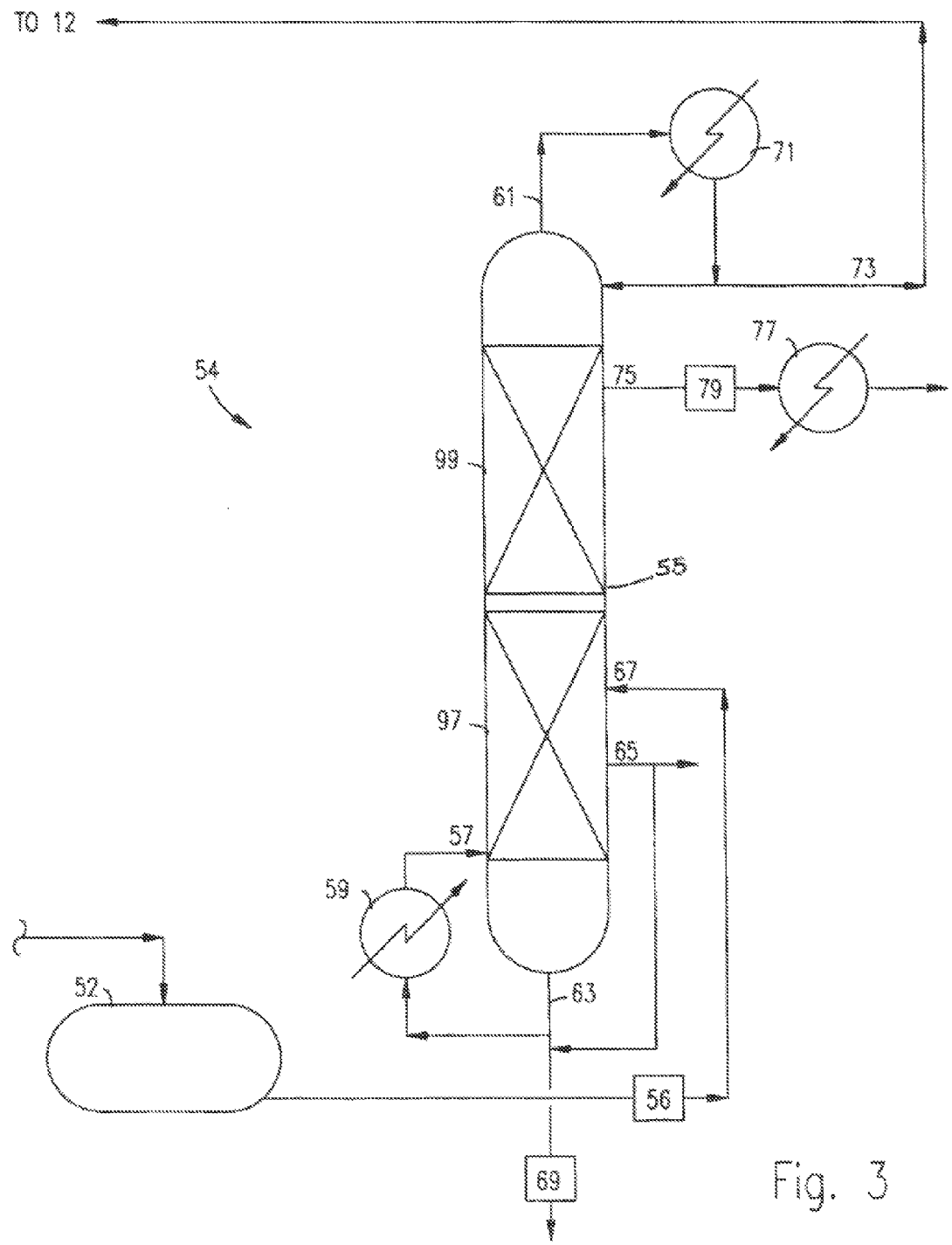
FIG. 3 is a schematic of the rectification section of the invention.

The feed enters rectification system 54 from surge tank 52, such as by rectification feed pump 56. The rectification column system 54 comprises two sections, namely a bottoms stripping section 97 and a top rectification section 99, as shown in FIG. 3. The feed is introduced to the stripping section 97 of column 55 and flows down through the packing, countercurrent to the stripping steam 57, which may be supplied by a rectification reboiler 59. The volatile component, including methanol, moves upward to the top rectification section 99, while the less volatile component, which is mainly water along with other high boilers, is removed as the underflow 63.

The feed may also comprise intermediate boilers, such as some higher alcohols (primarily ethanol), higher ketones, etc. These components, often referred to as fusel oils, are drawn off from the bottoms column 55, preferably at a point 65 located below the feed introduction point 67. The fusel oils can be recovered separately, or may be combined with the underflow 63 from the column 55, passing to effluent treatment through rectification bottoms pump 69.

The overhead vapour flow 61, comprising methanol and other volatiles, from upper rectification section 99 is condensed in a rectification reflux condenser 71, located above column 55. Any low boilers and non-condensables 73 may be vented to the incineration system 12.

The remaining product, which is approximately 99.85 wt % methanol, is drawn off in a stream 75, preferably located slightly below the top of the packing in top rectification section 99, and moved to a methanol cooler 77 by suitable means such as by methanol pump 79, where it can be moved to storage. The methanol product is preferably drawn off in sufficient quantities to maintain the methanol profile in the column.

Figure 4:
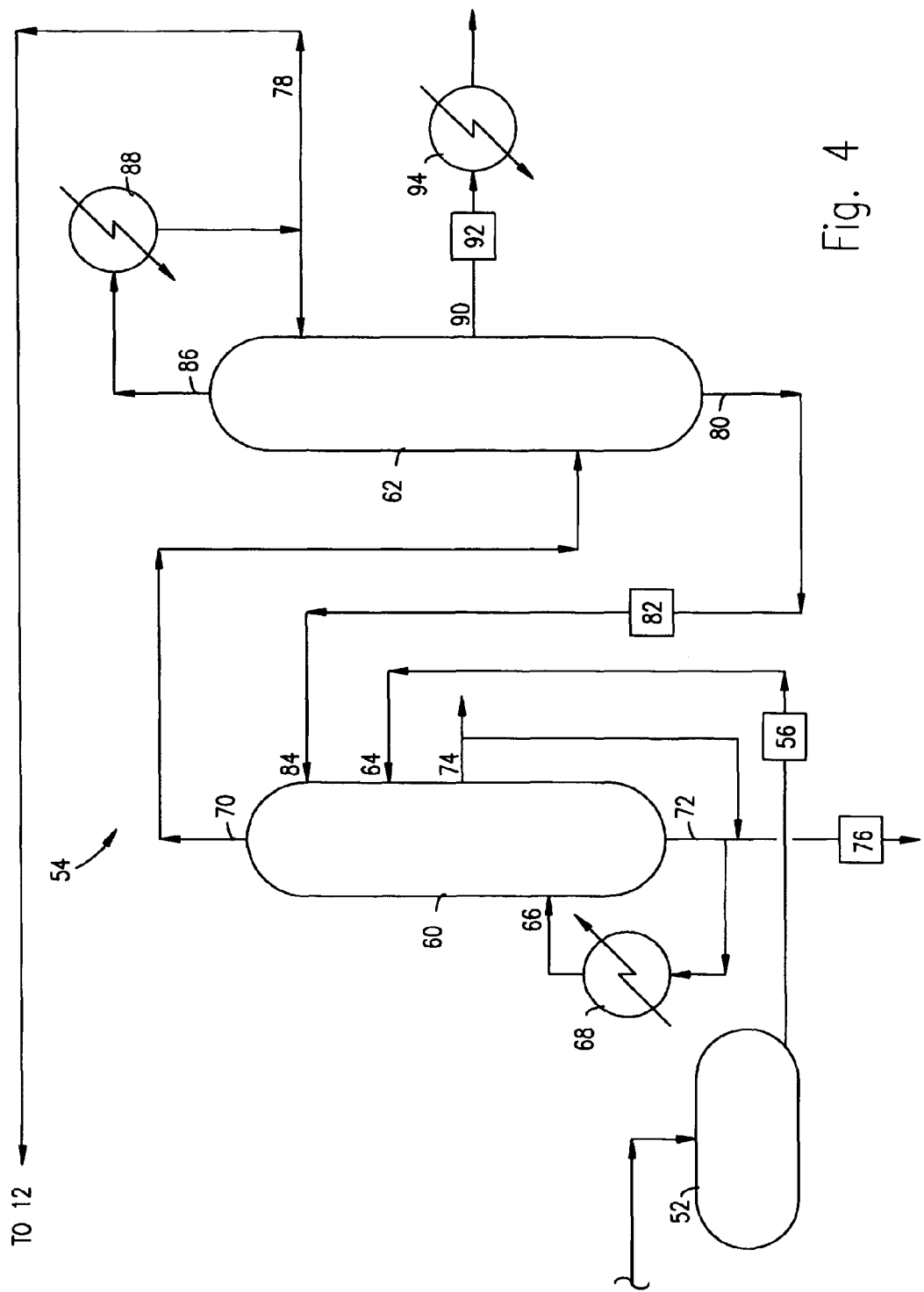
FIG. 4 is a schematic of an alternative layout of the rectification section of the invention.

Alternatively, the two sections of rectification column system 54 may be supplied in two separate columns, the rectification bottoms column 60 and the rectification top column 62, as shown in FIG. 4. The feed is introduced 64 to the stripping section of the bottoms column 60 and flows down through the packing, countercurrent to the stripping steam 66, which may be supplied by a rectification reboiler 68. The volatile component, including methanol, is removed into the overhead vapour flow 70, while the less volatile component, which is mainly water along with other high boilers, is removed as the underflow 72.

In this embodiment, the fusel oils are drawn off from the bottoms column 60, preferably at a point 74 located below the feed introduction point 64. Again, the fusel oils can be recovered separately, or may be combined with the underflow 72 from the column 60, passing to effluent treatment through rectification bottoms pump 76.

The overhead vapour flow 70 from rectification bottoms column 60 is directed to the lower section of the rectification top column 62. Any condensate 80 collected in the bottom of the top column 62 may be returned by an intermediate rectification pump 82 to introduction point 84 of the bottoms column 60. Vapour 86 from the top column 62 is condensed in a rectification reflux condenser 88, located above top column 62. Any low boilers and non-condensables 78 may be vented to the incineration system 12.

The remaining product, which is approximately 99.85 wt % methanol, is drawn off in a stream 90, preferably located slightly below the top of the packing in top column 62. Again, the methanol product is preferably drawn off in sufficient quantities to maintain the methanol profile in the column and moved to the methanol cooler 94 by suitable means such as by methanol pump 92, where it can be moved to storage.

It will be appreciated by those skilled in the art that other variations to the preferred embodiment described herein may be practiced without departing from the scope of the invention, such scope being properly defined by the following claims.

What is claimed is:

1. An apparatus to recover and purify methanol from a stripped off gas stream, comprising:
    a condenser to receive and condense a controlled amount of stripped off gas comprising no more than approximately 40 wt % methanol;
    a decanter to remove immiscible contaminants from said condensed gas;
    a first distiller comprising an input point to receive an acid feed and an entry point to receive said condensed gas, wherein said input point is lower than said entry point, said first distiller being configured to heat said condensed gas in the presence of said acid feed, to evaporate volatile components, leaving contaminated methanol;
    a first refining section to evaporate methanol from said contaminated methanol; and a second refining section to evaporate and condense impurities from said evaporated methanol, producing purified methanol.

2. The apparatus of claim 1, further comprising a storage tank to store said contaminated methanol prior to entering said first refining section.

3. The apparatus of claim 1, further comprising means to capture and condense said purified methanol for storage.

4. The apparatus of claim 1, further comprising means to remove fusel oils from said contaminated methanol.

5. The apparatus of claim 1, further comprising a diversion section to divert excess gas to a disposal system prior to entering said condensing means.

6. The apparatus of claim 1, wherein said first distiller comprises a topping column.

7. The apparatus of claim 6, wherein said topping column further comprises a reboiler to recycle part of said contaminated methanol.

8. The apparatus of claim 1, wherein said first and second refining sections comprise a second distiller.

9. The apparatus of claim 8 wherein said second distiller comprises a rectification column.

10. The apparatus of claim 8, wherein said second distiller comprises first and second rectification columns.

\* \* \* \* \*